(12) United States Patent
Christopher

(10) Patent No.: US 6,860,264 B2
(45) Date of Patent: Mar. 1, 2005

(54) METHOD AND APPARATUS FOR ENDOTRACHEAL INTUBATION USING A LIGHT WAND AND CURVED GUIDE

(75) Inventor: Kent L. Christopher, Denver, CO (US)

(73) Assignee: Evergreen Medical Incorporated, Denver, CO (US)

( * ) Notice: Subject to any disclaimer, the term of this patent is extended or adjusted under 35 U.S.C. 154(b) by 146 days.

(21) Appl. No.: 10/115,224

(22) Filed: Apr. 2, 2002

(65) Prior Publication Data

US 2002/0108610 A1 Aug. 15, 2002

Related U.S. Application Data

(63) Continuation-in-part of application No. 09/908,380, filed on Jul. 18, 2001, now Pat. No. 6,668,821, which is a continuation-in-part of application No. 09/840,194, filed on Apr. 23, 2001, now Pat. No. 6,634,354, which is a continuation-in-part of application No. 09/767,272, filed on Jan. 22, 2001, now Pat. No. 6,568,388, which is a continuation-in-part of application No. 09/707,350, filed on Nov. 6, 2000, now Pat. No. 6,543,446, which is a continuation-in-part of application No. 09/411,610, filed on Oct. 1, 1999, now Pat. No. 6,405,725, which is a continuation-in-part of application No. 08/974,864, filed on Nov. 20, 1997, now Pat. No. 5,964,217, which is a continuation of application No. 08/607,332, filed on Feb. 26, 1996, now Pat. No. 5,694,929.
(60) Provisional application No. 60/252,347, filed on Nov. 20, 2000.

(51) Int. Cl.[7] ............................................. A61M 16/00
(52) U.S. Cl. ............................. 128/200.26; 128/207.14; 128/207.15; 600/120
(58) Field of Search .......... 128/200.21, 207.14–207.18; 600/120, 194, 199

(56) References Cited

U.S. PATENT DOCUMENTS 4,244,362 A    1/1981   Anderson
4,444,185 A    4/1984   Shugar
4,567,882 A    2/1986   Heller
4,740,047 A  * 4/1988   Abe et al. ..................... 385/84
4,846,153 A  * 7/1989   Berci ......................... 600/109
5,131,380 A  * 7/1992   Heller et al. ................. 604/524
5,163,941 A   11/1992   Garth et al.

(List continued on next page.)

OTHER PUBLICATIONS

Orlando R. Hung, M.D., et al., "Clinical Trial of a New Lightwand Device (Trachlight) to Intubate the Trachea", Anesthesiology, Sep. 1995, pp. 509–514, vol. 83, No. 3, Lippincott–Raven Publishers.

Orlando R. Hung MD FRCPC, et al., "Light–guided retrograde intubation", Canadian Journal of Anaesthesia, 1997, pp. 877–882, vol. 44, No. 8.

Orlando Ricardo Hung MD FRCPC et al., "Lightwand intubation: I—A new lightwand device", Canadian Journal of Anaesthesia, 1995, pp. 820–825, vol. 42, No. 9.

Orlando R. Hung MD et al., "Lightwand intubation: II—Clinical trial of a new lightwand for tracheal intubation in patients with difficult airways", Canadian Journal of Anaethesia, 1995, pp. 826–830, vol. 42, No. 9.

*Primary Examiner*—Henry Bennett
*Assistant Examiner*—Amanda R. Flynn
(74) *Attorney, Agent, or Firm*—Dorr, Carson, Sloan, Birney & Kramer, P.C.

(57) ABSTRACT

A method and apparatus for endotracheal intubation with simultaneous oxygenation/ventilation employs a curved guide and a light wand to ensure proper placement of the endotracheal tube in the patient's airway. The light wand has an elongated flexible member with a light source at its distal tip. The wand is inserted through an endotracheal tube until the light is adjacent to the distal end of the endotracheal tube. A curved guide is inserted into the patient's mouth and upper airway so that its distal end is positioned above the larynx. The wand and endotracheal tube are then advanced along the guide until the distal end of the endotracheal tube passes through the larynx and the light source is externally observable at a predetermined location through the anterior tracheal wall.

17 Claims, 12 Drawing Sheets

U.S. PATENT DOCUMENTS

| | | | | |
|---|---|---|---|---|
| 5,273,029 A | * | 12/1993 | Wilk et al. | 128/200.26 |
| 5,280,788 A | * | 1/1994 | Janes et al. | 600/476 |
| 5,285,778 A | * | 2/1994 | Mackin | 128/207.15 |
| 5,327,881 A | * | 7/1994 | Greene | 600/120 |
| 5,329,940 A | * | 7/1994 | Adair | 128/200.26 |
| 5,363,838 A | | 11/1994 | George | |
| 5,390,661 A | * | 2/1995 | Griffith et al. | 600/114 |
| 5,423,321 A | * | 6/1995 | Fontenot | 600/476 |
| 5,431,152 A | | 7/1995 | Flam et al. | |
| 5,560,351 A | | 10/1996 | Gravenstein et al. | |
| 5,636,625 A | * | 6/1997 | Miyagi et al. | 128/200.26 |
| 5,672,179 A | | 9/1997 | Garth et al. | |
| 5,676,635 A | * | 10/1997 | Levin | 600/120 |
| 5,694,929 A | * | 12/1997 | Christopher | 128/207.14 |
| 5,733,242 A | | 3/1998 | Rayburn et al. | |
| 5,775,322 A | * | 7/1998 | Silverstein et al. | 128/207.14 |
| 5,913,816 A | * | 6/1999 | Sanders et al. | 600/120 |
| 5,921,917 A | * | 7/1999 | Barthel et al. | 600/120 |
| 5,941,816 A | * | 8/1999 | Barthel et al. | 600/120 |
| 5,964,217 A | * | 10/1999 | Christopher | 128/200.26 |
| 6,081,741 A | | 6/2000 | Hollis | |
| 6,161,537 A | | 12/2000 | Gravenstein et al. | |
| 6,196,225 B1 | * | 3/2001 | Allgeyer | 128/207.15 |
| 6,543,446 B1 | * | 4/2003 | Christopher | 128/200.26 |
| 2003/0188750 A1 | * | 10/2003 | Christopher | 128/207.14 |
| 2004/0079264 A1 | * | 4/2004 | Mayerle et al. | 111/174 |

* cited by examiner

Fig. 13
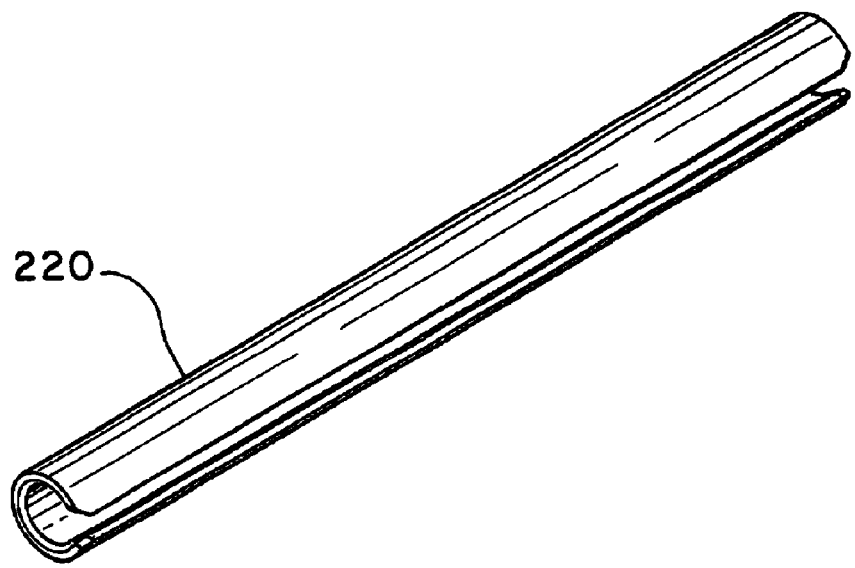
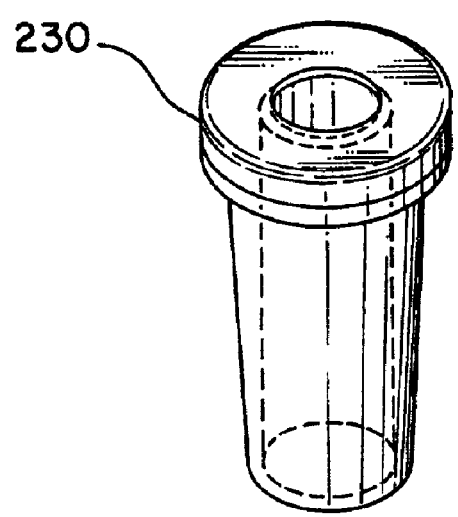
Fig. 14

METHOD AND APPARATUS FOR ENDOTRACHEAL INTUBATION USING A LIGHT WAND AND CURVED GUIDE

RELATED APPLICATIONS

The present application is a continuation-in-part of the Applicant's U.S. patent application Ser. No. 09/908,380, entitled "Laryngeal Mask Airway," filed on Jul. 18, 2001, now U.S. Pat. No. 6,668,821 which is a continuation-in-part of U.S. patent application Ser. No. 09/840,194, filed on Apr. 23, 2001, now U.S. Pat. No. 6,634,354 which claims priority to U.S. Provisional Patent Application Ser. No. 60/252,347, filed on Nov. 20, 2000. The present application is also a continuation-in-part of the Applicant's U.S. patent application Ser. No. 09/767,272, entitled "Method and Apparatus for Ventilation/Oxygenation During Guided Insertion of an Endotracheal Tube," filed on Jan. 22, 2001, now U.S. Pat. No. 6,568,388 which is a continuation-in-part of U.S. patent application Ser. No. 09/707,350, filed on Nov. 6, 2000, now U.S. Pat. No. 6,543,446 which is a continuation-in-part of U.S. patent application Ser. No. 09/411,610, filed on Oct. 1, 1999, now U.S. Pat. No. 6,405,725 which is a continuation-in-part of U.S. patent application Ser. No. 08/974,864, filed on Nov. 20, 1997, now U.S. Pat. No. 5,964,217, issued on Oct. 12, 1999, which is a continuation of U.S. patent application Ser. No. 08/607,332, filed on Feb. 26, 1996, now U.S. Pat. No. 5,694,929, issued on Dec. 9, 1997.

BACKGROUND OF THE INVENTION

1. Field of the Invention

The present invention relates generally to the field of tracheal intubation. More specifically, the present invention discloses a method and apparatus for intubating a patient with an endotracheal tube that uses a curved guide and a flexible light wand to ensure proper placement of the endotracheal tube.

2. Statement of the Problem

Endotracheal tubes are used in semi-emergency situations to ventilate patients with respiratory failure who may be conscious or semi-conscious. The conventional approach requires the patient to lie still while the physician inserts a rigid laryngoscope blade into the patient's mouth and trachea. Delivery of ventilation and/or oxygen is also interrupted during this period. The endotracheal tube is then inserted into place while the laryngoscope blade keeps the patient's airway open. Successful intubation depends on the patient being cooperative and completely relaxed, which unfortunately is often not the case. Even with a cooperative patient, intubation is very uncomfortable and can cause the patient to panic due to the difficulty in breathing during the procedure. This procedure can also result in a choking or gagging response that can cause the patient to regurgitate and aspirate contents from the stomach. One conventional response to these shortcomings has been to sedate the patient during intubation. Tranquilizers make the patient more cooperative and less likely to choke during intubation, but also tend to suppress the patient's breathing and blood pressure. These side effects may be unacceptable when dealing with a patient who already suffers from shallow or irregular breathing or depressed blood pressure. Therefore, a need exists for an improved device to guide insertion of an endotracheal tube and ensure the patient's airway is open, and that also allows the patient to continue to receive air/oxygen during the insertion process.

In addition, a separate but related problem exists because of the difficulty in advancing the distal end of the endotracheal tube through the patient's larynx and into the appropriate position in the trachea. The tissues of the larynx and trachea can be easily traumatized by the endotracheal tube or insertion guide. One common approach to this problem has been to insert a endoscopic probe through the endotracheal tube, and then advance both the endoscopic probe and endotracheal tube along the patient's airway. The healthcare provider can view through the endoscope and control the direction of the distal tip of the endoscope probe to guide the endotracheal tube into proper position. However, an endoscope typically costs several thousand dollars. In addition, the endoscope probe is relatively delicate and can be difficult to sterilize after use.

The prior art in this field includes several devices that use a light source on distal end of a wand to indicate the location of the distal end of the endotracheal tube. The tissue on the anterior side of the trachea below the larynx is relatively thin. If a small light source is placed adjacent to the anterior wall of the trachea below the larynx, it can typically be seen by the healthcare provider as a faint glow emanating through the anterior tracheal wall. Although an endoscope has the advantage of enabling the healthcare provider to guide and view the intubation process, the price of a light wand is a small fraction of that of an endoscope. In fact, a light wand can be made to be disposable. A light wand also has the advantages of being small, lighter, and easier to store in situations were space is limited, such as in an ambulance.

Laerdal Medical Corporation of Armonk, N.Y., markets the "Trachlight" light wand. This device has a removable metal stylet that is inserted into a flexible light wand and then bent into the general shape of a hockey stick. The light wand assembly is then inserted into an endotracheal tube, and both are advanced along the patient's airway to a position above the larynx. To minimize the risk of injury to the larynx, the stylet is then withdrawn from within the light wand. The distal ends of the endotracheal tube and light wand are then advanced through the larynx and into the trachea without the structural support of the stylet. The light source at the end of the light wand becomes visible to the healthcare provider by transillumination of the trachea when the light wand and endotracheal tube are advanced to the appropriate positions in the trachea.

A light wand is also currently marketed by Vital Signs, Inc. having a non-removable stylet. Here again, there is a risk that the rigid light wand or endotracheal tube will injure the larynx or trachea.

3. Solution to the Problem

None of the prior art discussed above show a flexible light wand to ensure proper placement of the distal end of the endotracheal tube, in combination with a curved guide that serves both to ventilate the patient and guide the endotracheal tube and light wand along the patient's airway and through the larynx. The present invention enables the patient to be ventilated during the intubation process. In addition, the curved guide eliminates the need for rigidity of the light wand and thereby reduces the risk of injury to the larynx or trachea.

SUMMARY OF THE INVENTION

This invention provides a method and apparatus for endotracheal intubation with simultaneous oxygenation/ventilation employing a curved guide and a light wand to ensure proper placement of the endotracheal tube in the patient's airway. The light wand has an elongated flexible member with a light source at its distal tip. The light wand is inserted through an endotracheal tube until the light is adjacent to the distal end of the endotracheal tube. A curved guide is inserted into the patient's mouth and upper airway so that its distal end is positioned above the larynx. The wand and endotracheal tube are then advanced along the guide until the distal end of the endotracheal tube passes through the larynx and the light source is externally observable at a predetermined location through the anterior tracheal wall.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which:

FIG. 13 is a perspective view of the stabilizer 220 that can be attached to the light wand 30.

FIG. 14 is a perspective view of the endotracheal tube cap 230 that can be used in conjunction with the stabilizer 220.

DETAILED DESCRIPTION OF THE INVENTION

Figure 1:
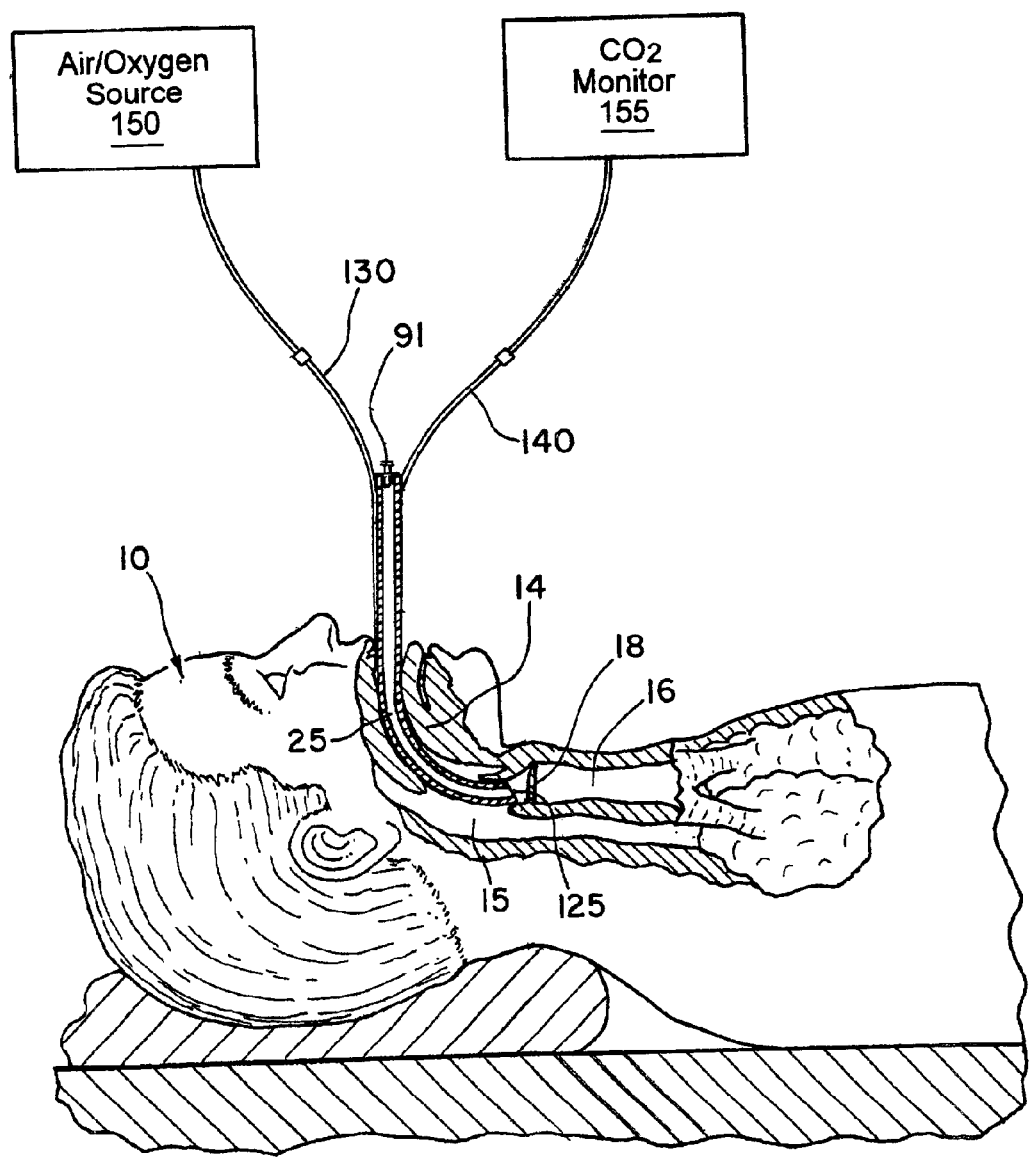
FIG. 1 is a cross-sectional view of the mouth and airway of a patient after the guide 25 has been inserted into the patient's mouth, over the tongue, and into the hypopharynx.
Figure 6:
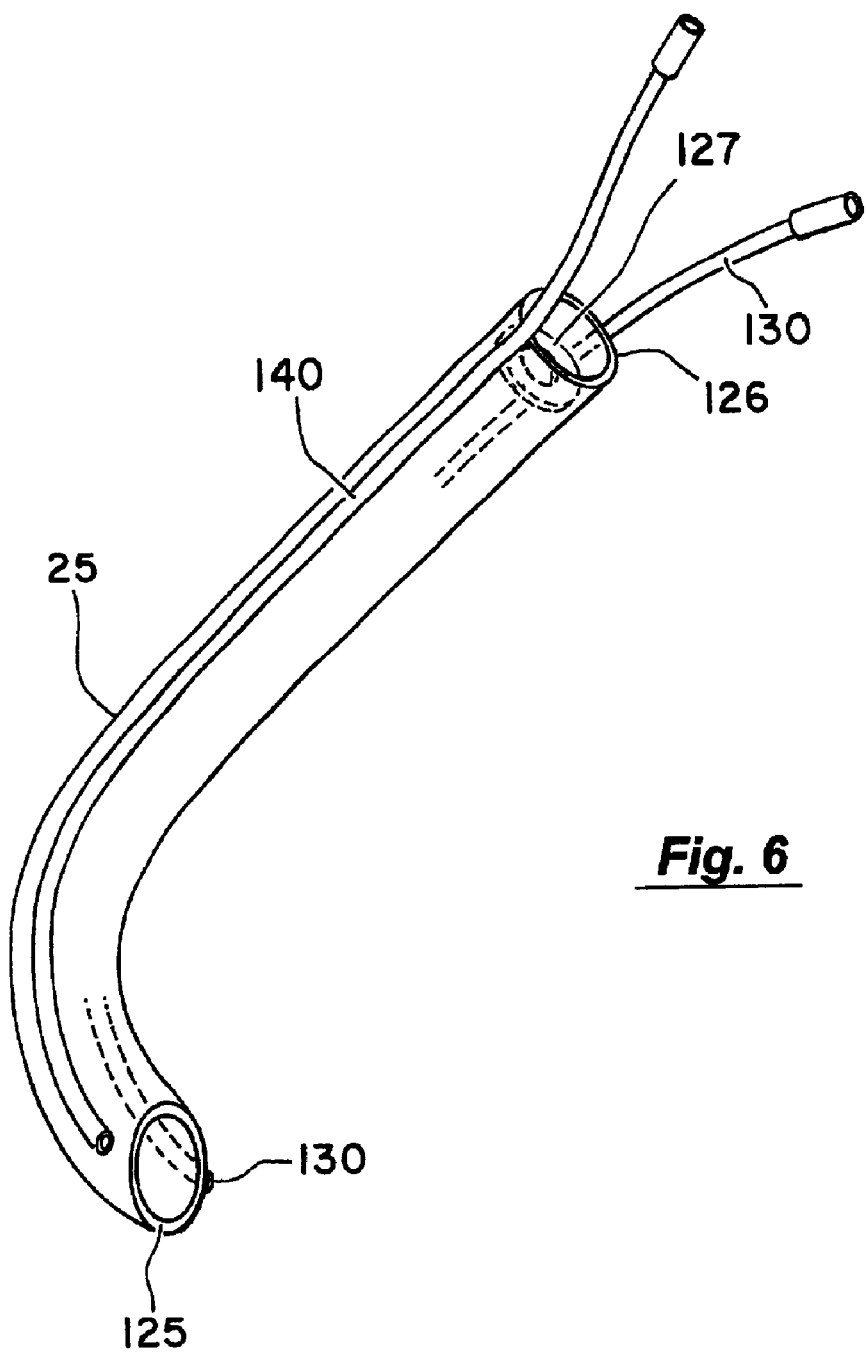
FIG. 6 is a front perspective view of the guide 25.

Turning to FIG. 1, a cross-sectional view is provided of the mouth and airway of a patient after the guide 25 has been inserted into the patient's mouth, over the tongue 14, and into the hypopharynx 15. A corresponding front perspective view of the guide 25 is shown in FIG. 6. The guide 25 is generally tubular and has a curved distal portion to follow the profile of a typical patient's airway through the mouth, over the tongue 14, and into the hypopharynx 15 just above the opening to the trachea 16. Although the guide 25 is generally J-shaped, it may be necessary to provide a variety of guides with different dimensions and profiles to accommodate variations in the size and shape of patient airways. Ideally, the guide 25 should extend from the patient's mouth and through the hypopharynx with its distal end immediately above the opening to the larynx 18. In particular, the guide 25 is shaped to prevent the patient's tongue 14 and collapsible pharynx from obstructing access to the trachea 16, while also defining a channel for later insertion of an endotracheal tube.

The guide 25 is typically made of plastic with sufficient strength and rigidity to keep the patient's teeth apart and prevent the patient from biting down on the endotracheal tube. In addition, the guide 25 should have a relatively low coefficient of friction to minimize irritation to the lining of mouth and trachea and to minimize resistance to insertion of an endotracheal tube along the guide. Friction can be further reduced by applying a slippery coating to both the exterior and interior surfaces of the guide 25. A slippery coating can also be applied to the endotracheal tube to minimize friction between the endotracheal tube and the guide. The distal end of the guide 25 can be beveled to ease insertion.

The guide 25 is equipped with a small second lumen 130 bonded to the exterior of the guide 25 that extends along the length of the guide 25. The second lumen 130 delivers a flow of air/oxygen for supplemental ventilation of the patient. Preferably, this lumen 130 extends to the distal tip of the guide 25 so that this supplemental air/oxygen can be delivered near the opening to the larynx 18 to flow through the opening between the vocal cords and into the patient's lungs.

The second lumen 130 can have any radial position relative to the central longitudinal axis of the guide. However, it is easier to align the flow exiting the second lumen 130 with the opening between the vocal cords if the second lumen 130 extends along the lateral portion of the guide 25 (e.g., at the 3 o'clock or 9 o'clock positions). In contrast, the second lumen 130 might tend to become obstructed with mucous or secretions if it is placed along the posterior or anterior portions of the guide 25. In addition, the tip of the second lumen 130 or the flow of air/oxygen might irritate the patient's airway in these configurations.

As shown in FIG. 6, the second lumen 130 can be a tube bonded to the exterior of the guide 25 so that it does not interfere with the endotracheal tube 40 as it is advanced along the interior passageway of the guide 25. Alternatively, the lumen can be placed within the guide or formed as a conduit in the wall of the guide. The lumen should have a diameter (or cross-sectional area) sufficient to support of flow rate of approximately 1 to 20 liters per minute with minimal back pressure.

A standard connector on the proximal end of the second lumen 130 allows it to be removably attached to a conventional air/oxygen source 150, as illustrated in FIG. 1. For example, the second lumen 130 can be connected to an oxygen line of the type commonly found in hospitals and other clinical settings. Alternatively, the second lumen 130 can be connected to a portable oxygen source or a ventilator, such as an anesthesia ventilator. Here again, a flow rate of approximately 1 to 20 liters per minute is preferable. For example, the flow can be provided on a continuous basis, in periodic pulses, or in a waveform simulating the patient's nature respiratory cycle. The flow of air/oxygen increases diffusion oxygenation within the alveoli to boost the patient's blood oxygen level, and also serves to flush carbon dioxide from the patient's lungs and airway. In addition, if the flow rate of oxygen supplied through the second lumen 130 is sufficiently high, oxygen will accumulate in the patient's upper airway and create a reservoir of oxygen that enhances the effectiveness of the patient's natural respiration.

Optionally, the guide 25 can be equipped with a third lumen 140 to sample and measure the chemical composition of gas in the patient's airway. For example, the third lumen can be used to monitor the concentration of carbon dioxide in the patient's airway. As shown in FIG. 6, the third lumen 140 extends along the lateral portion of the guide 25 opposite from the second lumen 130 to minimize the affect of the air/oxygen supplied via the second lumen 130 on the accuracy of the carbon dioxide measurement. In the preferred embodiment depicted in FIG. 6, the distal end of the third lumen 140 terminates short of the distal end of the guide 25 to further enhance the accuracy of the carbon dioxide measurement.

The carbon dioxide concentration in a patient's airway can vary widely over the patient's respiratory cycle. Due to the physiological dead space in the patient's airway, measurements taken at the end of exhalation in the respiratory cycle (i.e., end-tidal measurements) tend to most accurately reflect the concentration of carbon dioxide in the lungs, and therefore most accurately reflect the concentration of carbon dioxide in the patient's blood stream.

Returning to FIG. 1, the proximal end of the third lumen 140 is fitted with a connector so that a carbon dioxide monitor 155 can periodical sample gas from the patient's airway via the third lumen 140 for analysis. As with the second lumen 130, the third lumen 140 can be a small tube bonded to the exterior of the guide 25, as shown in the accompanying drawings. Alternatively, it can be bonded to the interior of the guide or formed as a conduit in the wall of the guide.

If necessary, the guide 25 can be equipped with additional lumens for other purposes. For example, a suction tube can be used to suction secretions from the patient's mouth and airway as the guide 25 is advanced. Alternatively a syringe 55 containing a local anesthetic (e.g., lidocaine or xylocaine) can be connected to the proximal end of an ancillary lumen to squirt anesthetic as the guide 25 is inserted through the patient's mouth and into the hypopharynx 15. If squirted with sufficient force, the anesthetic can be carried as far as the larynx 18 to deaden any discomfort associated with insertion of the endotracheal tube 40. The main lumen of the guide 25 can also be used for suctioning secretions from the patient's mouth and airway, if necessary.

During and after insertion of the guide 25, air/oxygen is supplied through the second lumen 130 to maintain the patient, as shown in FIG. 1. If necessary, a removable cap 91 can be used to temporarily seal the proximal end of the guide 25. This guide cap 91 has an outside diameter dimensioned to seat into the proximal opening of the guide 25. A central passageway extends through the guide cap 91. A luer connector with a one-way valve (e.g., a duck-bill valve) is permanently attached to the guide cap 91 so that air or fluid can only flow down the passageway of the guide cap 91, but not up. Thus, the one-way valve 193 serves to prevent air/oxygen from escaping through the guide 25 during initial resuscitation. Optionally, a syringe containing anesthetic can be secured to the luer connector on the guide cap. As the guide 25 is advanced into the patient's mouth and hypopharynx, the healthcare provider squirts anesthetic from the syringe, through the one-way valve and guide 25 to lessen discomfort.

Figure 5:
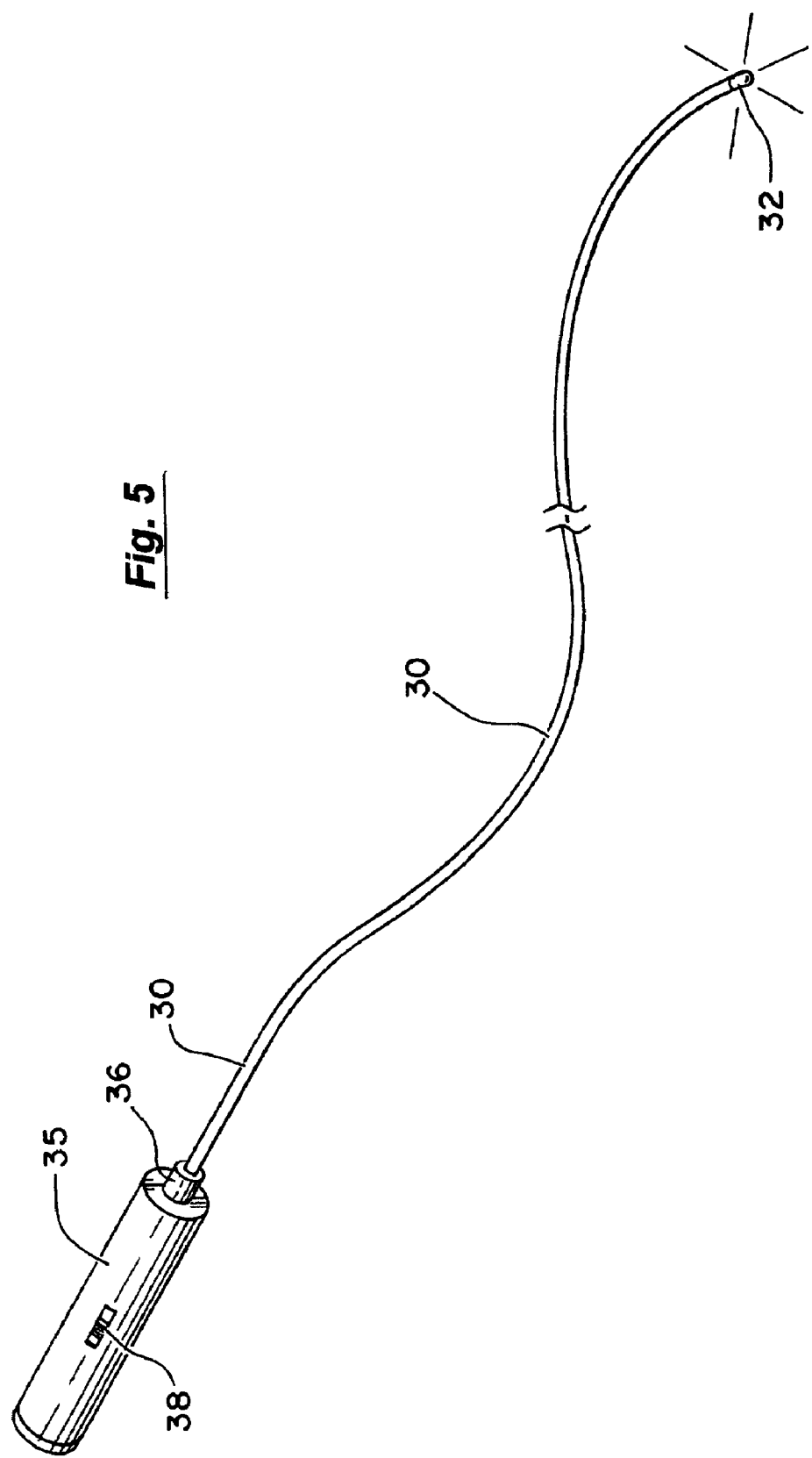
FIG. 5 is a perspective view of the light wand 30 and its detachable handle 35.

In the present invention, a light wand 30 is initially inserted through the endotracheal tube 40 before it is advanced along the guide 25. In the preferred embodiment, the distal tip of the light wand 30 is inserted through the endotracheal tube until it is adjacent to the tip of the endotracheal tube 40. FIG. 5 is a perspective view of one embodiment of the light wand 30. The light wand 30 has a light source 32 at the distal tip of a flexible, elongated member with an outside diameter small enough to fit through a conventional endotracheal tube. The distal tip of the light wand 30 is also flexible and atraumatic, unlike the prior art, to minimize the risk of injury to the patient's airway. The guide 25 serves the function of the stylet in the prior art to guide and support the endotracheal tube 40 and light wand 30 during intubation. The light source 32 is powered by batteries stored in its handle 35. For example, the light source can be housed in the handle 35 with a series of optical fibers leading to the distal tip of the wand 30. Alternatively, a small light bulb or light-emitting diode could be placed on the distal tip of the wand 30 and connected by wires to batteries in the handle 35. The light source 32 is controlled by an on/off switch 38 on the handle 35. In the preferred embodiment of the light wand 30, the handle 35 can be detached from the remainder of the wand 30 by unplugging a connector 36 shown in FIG. 5. This simplified cleaning and sterilization of the unit.

Optionally, the light wand 30 can be equipped with a timer that provides an visual or audible indicia triggered a predetermined time period following activation of the light source. For example, the light wand can be designed to emitting a beeping noise or flash the light source 32 after a predetermined period of time. This provides a warning to the healthcare provider that the intubation process is taking too long.

Figure 2:
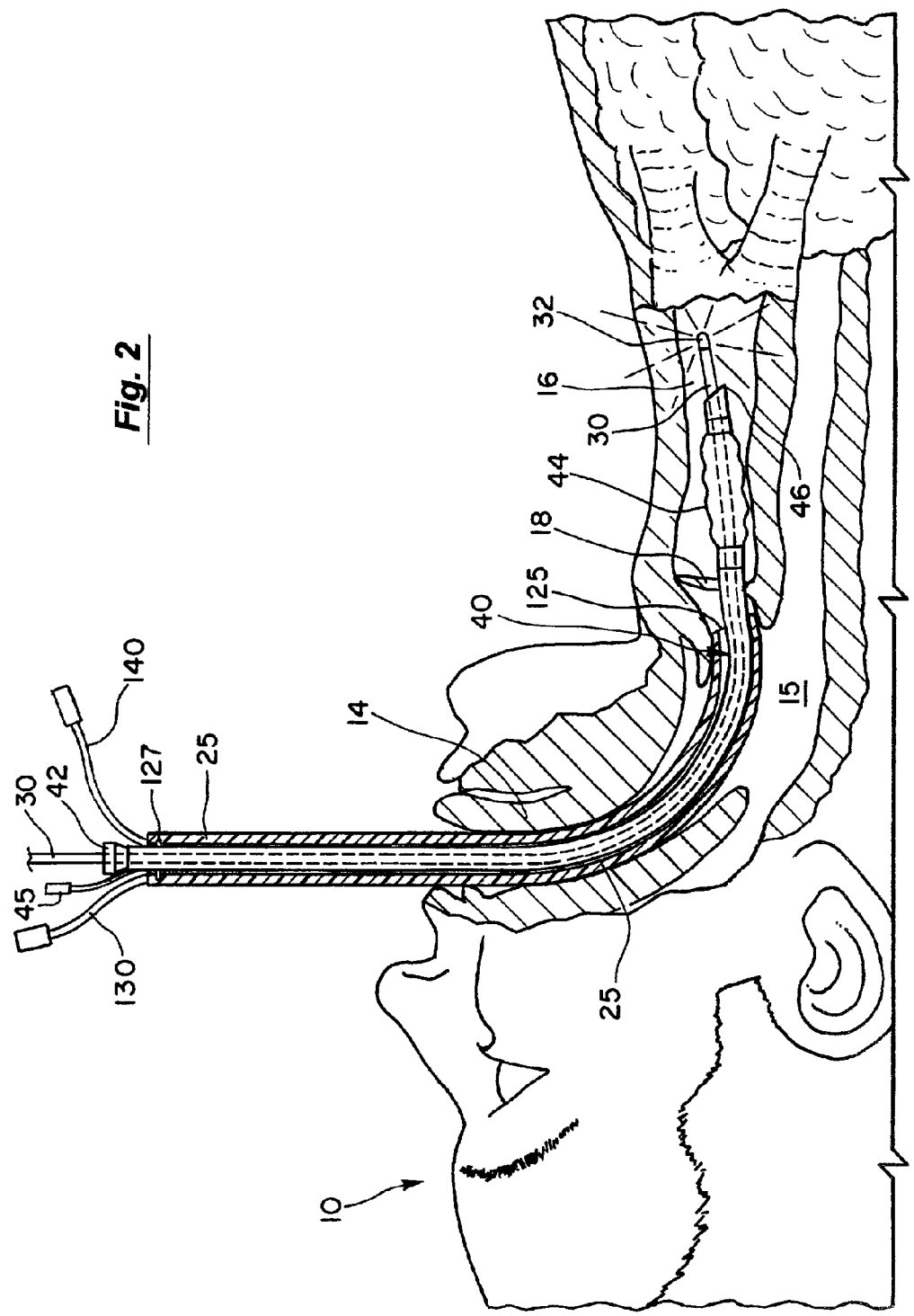
FIG. 2 is a cross-sectional view of the mouth and airway of the patient corresponding to FIG. 1 after the light wand 30 and endotracheal tube 40 have been advanced along the guide 25 to a position below the larynx.

After the endotracheal tube 40 has been inserted over the light wand 30, the guide cap 91 is removed from the guide 25. The light wand 30 and endotracheal tube 40 are then inserted along the guide 25 to a position within the trachea 16 past the larynx 18 while the flow of air/oxygen continues through the second lumen 130. FIG. 2 is a cross-sectional view of the mouth and airway of the patient corresponding to FIG. 1 after the light wand 30 and endotracheal tube 40 have been advanced along the guide 25 to a position below the larynx 18. In the preferred embodiment, an annular ring 127 within the proximal end of the guide 25 forms a loose seal around the endotracheal tube 40 to help prevent potentially contaminated respiratory secretions from being sprayed up at the physician between the guide 25 and the endotracheal tube 40.

The distal end 46 of the endotracheal tube 40 can be beveled as illustrated in FIG. 2. Experience has shown that injury to the larynx 18 can be reduced by spinning the endotracheal tube 40 as it is advanced. The beveled end tends to keep the endotracheal tube 40 centered as it is passes through the vocal cords. Injury to the lining of the mouth and trachea can be reduced by using an endotracheal tube 40 made of a material having a low coefficient of friction, such as silicone. Bivona Medical Technologies of Gary, Ind., markets a line of endotracheal tubes made of silicone with a helical reinforcing wire.

Figure 3:
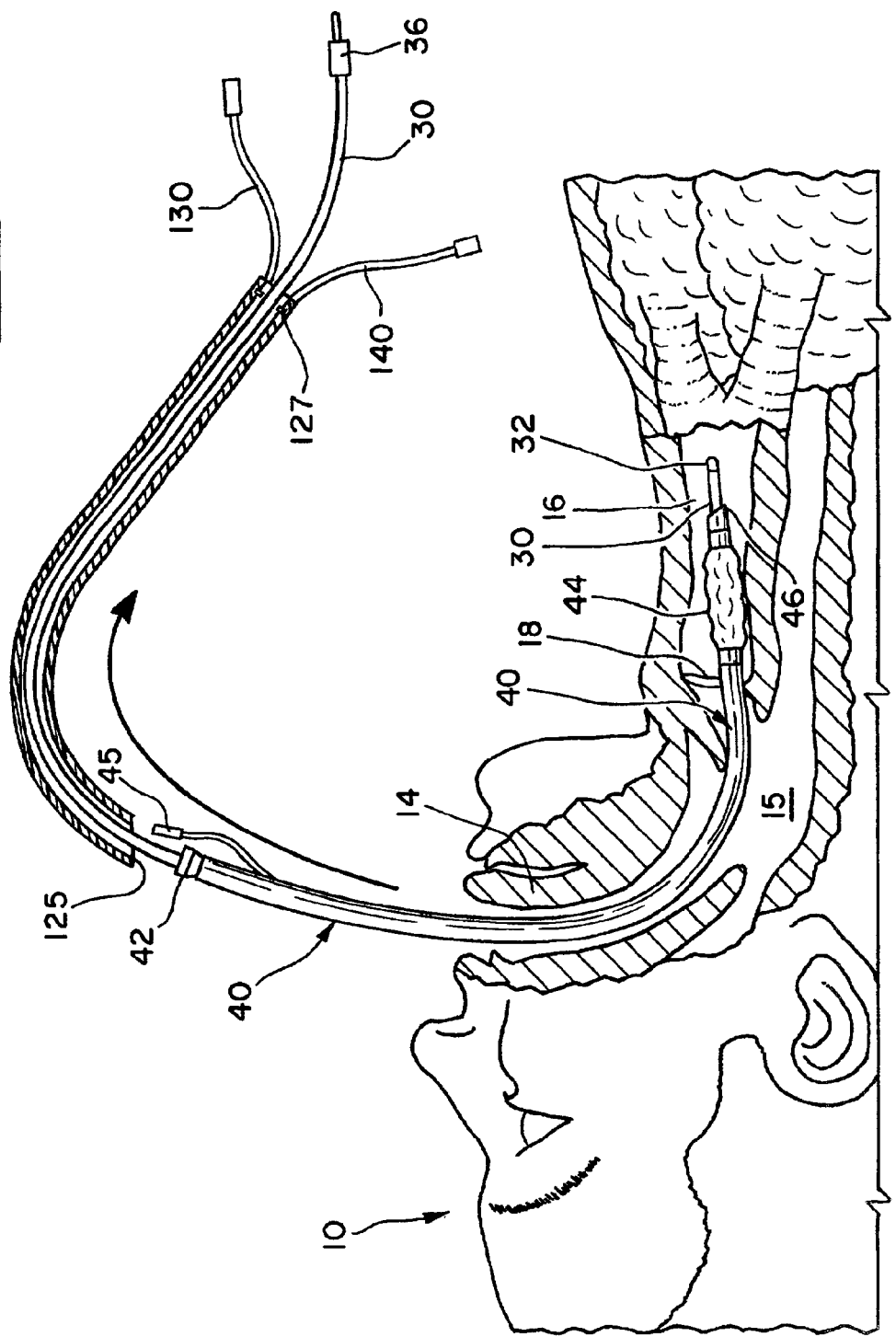
FIG. 3 is a cross-sectional view of the mouth and airway of the patient corresponding to FIGS. 1 and 2 after the guide 25 has been retracted over the endotracheal tube 40 and light wand 30.

After the endotracheal tube 40 and light wand 30 have been moved into position with their distal ends in the trachea 16, the light source 32 at the distal tip of the light wand will create a glow emanating through the anterior wall of the trachea 16 that is visible to the healthcare provider. The guide 25 can then be removed over the proximal end of the endotracheal tube 40 while leaving the endotracheal tube 40 and light wand 30 in place, as shown in FIG. 3. FIG. 3 is a cross-sectional view of the mouth and airway of the patient corresponding to FIGS. 1 and 2 after the guide 25 has been retracted over the endotracheal tube 40 and light wand 30. In the preferred embodiment, the flexible member of the light wand 30 is designed with sufficient length to allow the guide 25 to be retracted over the light wand 30 while leaving the endotracheal tube 40 in place in the patient's airway. Alternatively, the guide 25 can be completely removed by disconnecting the handle 35 from the wand 30, so that the guide 25 can be retracted over the endotracheal tube 40 and removed over the proximal end of the disconnected flexible member of the wand 30. In this embodiment, the flexible member of the light wand 30 can be disposable to eliminate cleaning and sterilization costs and prevent the risk of contamination associated with re-use of a light wand.

The position of the distal end of the endotracheal tube 40 can be monitored by the healthcare provider by watching the position of the glow produced by the light source 32 of the wand 30 relative to the patient's anatomy. The light wand 30 is then withdrawn from within the endotracheal tube 30.

Figure 4:
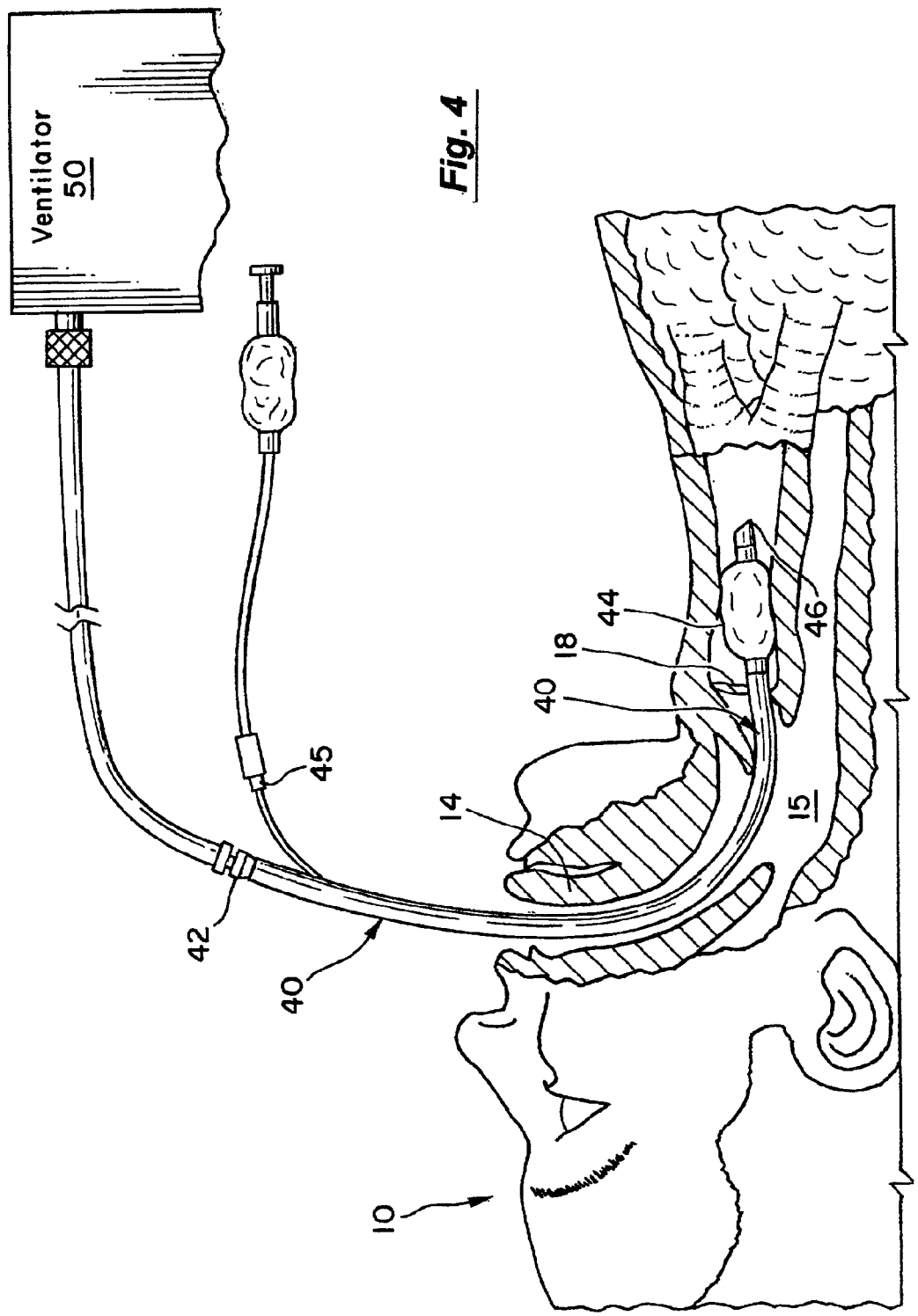
FIG. 4 is a cross-sectional view of the mouth and airway of the patient corresponding to FIG. 1 after the light wand 30 and guide 25 have been removed, the endotracheal tube cuff 44 has been inflated, and a ventilator 50 has been connected to the endotracheal tube 40.

After the guide 25 and light wand 30 have been removed, the endotracheal tube 40 is taped to the patient's face or held in place by some other suitable means for attachment. Alternatively, the guide 25 can be left in place to serve as an oral airway and to protect the endotracheal tube 40 from being bitten by the patient's teeth. The cuff 44 at the distal end 46 of the endotracheal tube 40 is then inflated through the port valve 45 to block the trachea 16. An external ventilator 50 is then attached to the connector 42 at the proximal end of the endotracheal tube 40, as shown in FIG. 4. The patient can then be mechanically ventilated in the conventional manner via the endotracheal tube 40. Alternatively, the patient can be manually ventilated by attaching a resuscitation bag to the connector 42 at the proximal end of the endotracheal tube.

It is important to note that the present invention allows the guide 25 to be inserted while the patient's head remains in a neutral position. Many conventional intubation blades and laryngoscopes require that the patient's head must be tipped back, which can be dangerous or difficult for patients with head or neck injuries or arthritis. In contrast, the guide 25 in the present invention has a curved distal portion to fit the upper airway without tipping the patient's head back.

Laryngeal Mask Airway.

Figure 7:
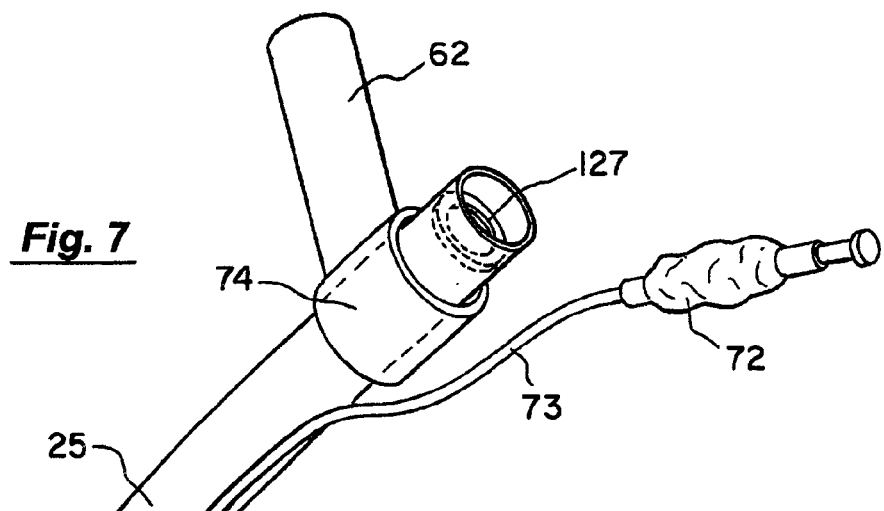
FIG. 7 is a front perspective view of another embodiment of the guide 25 that includes a laryngeal mask 70 and a rotatable collar 74 for delivery of air/oxygen through the guide 25.
Figure 8:
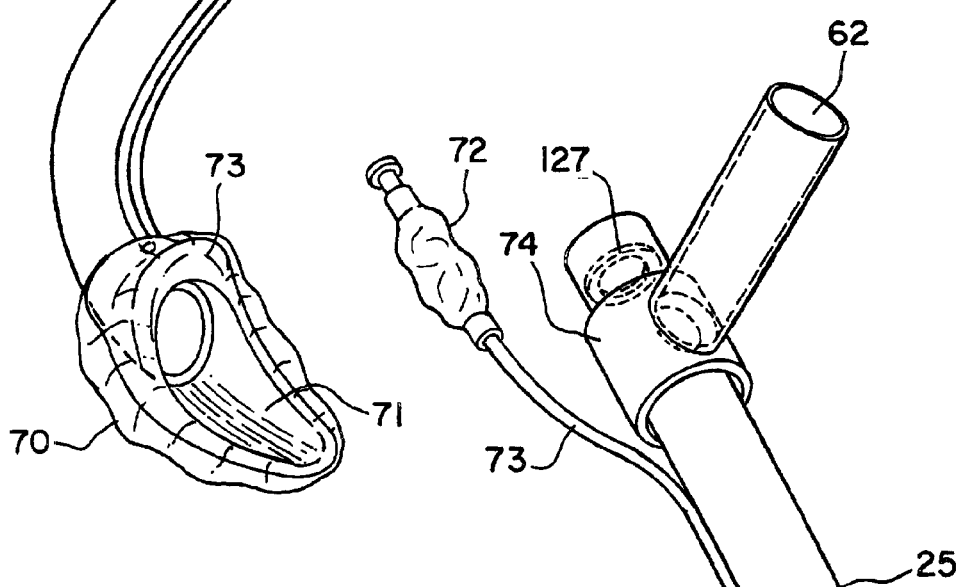
FIG. 8 is a rear perspective view of the guide 25 corresponding to FIG. 7.
Figure 9:
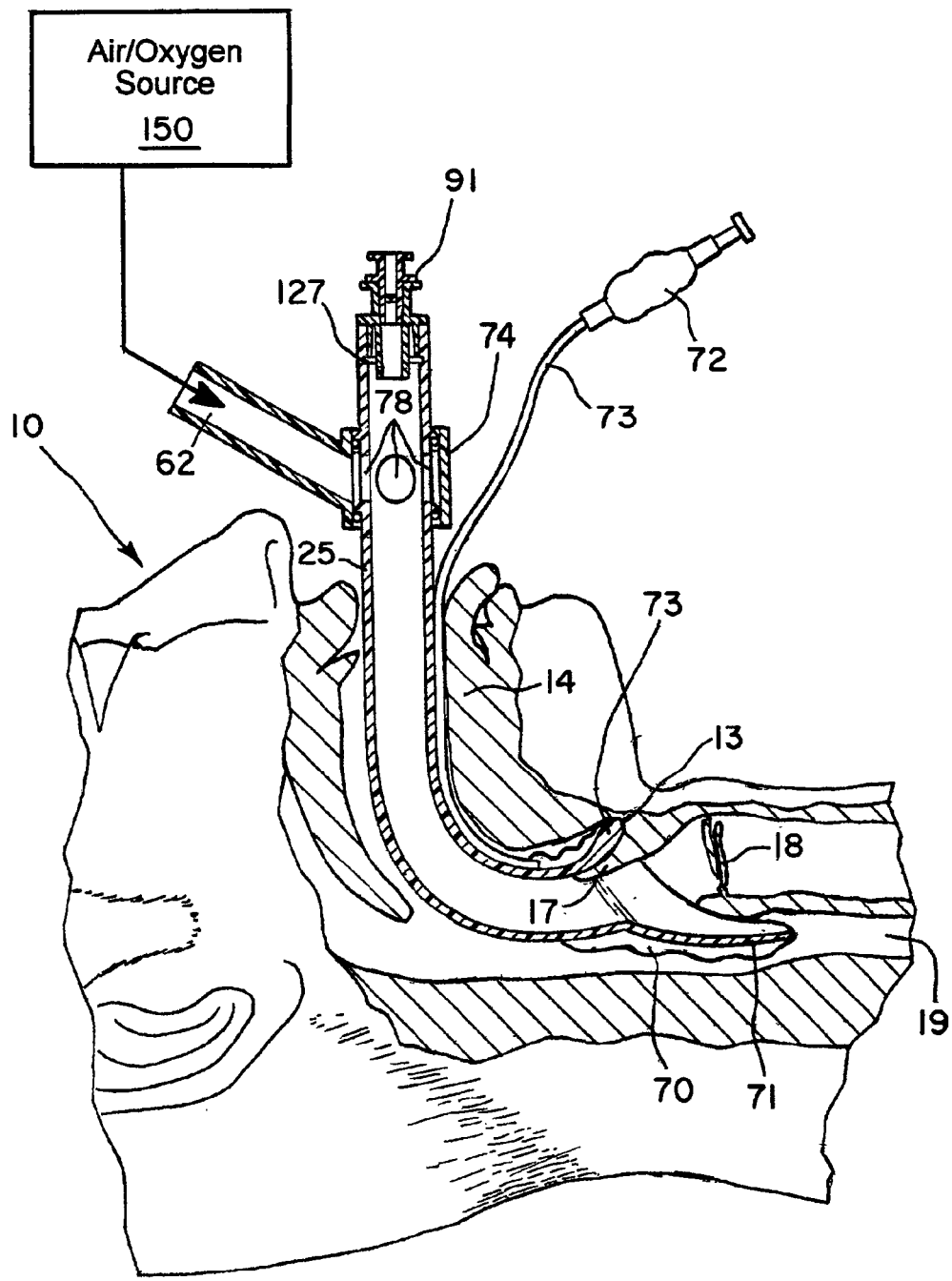
FIG. 9 is a cross-sectional view of a patient's airway after the guide 25 shown in FIGS. 7–8 has been initially inserted.
Figure 10:
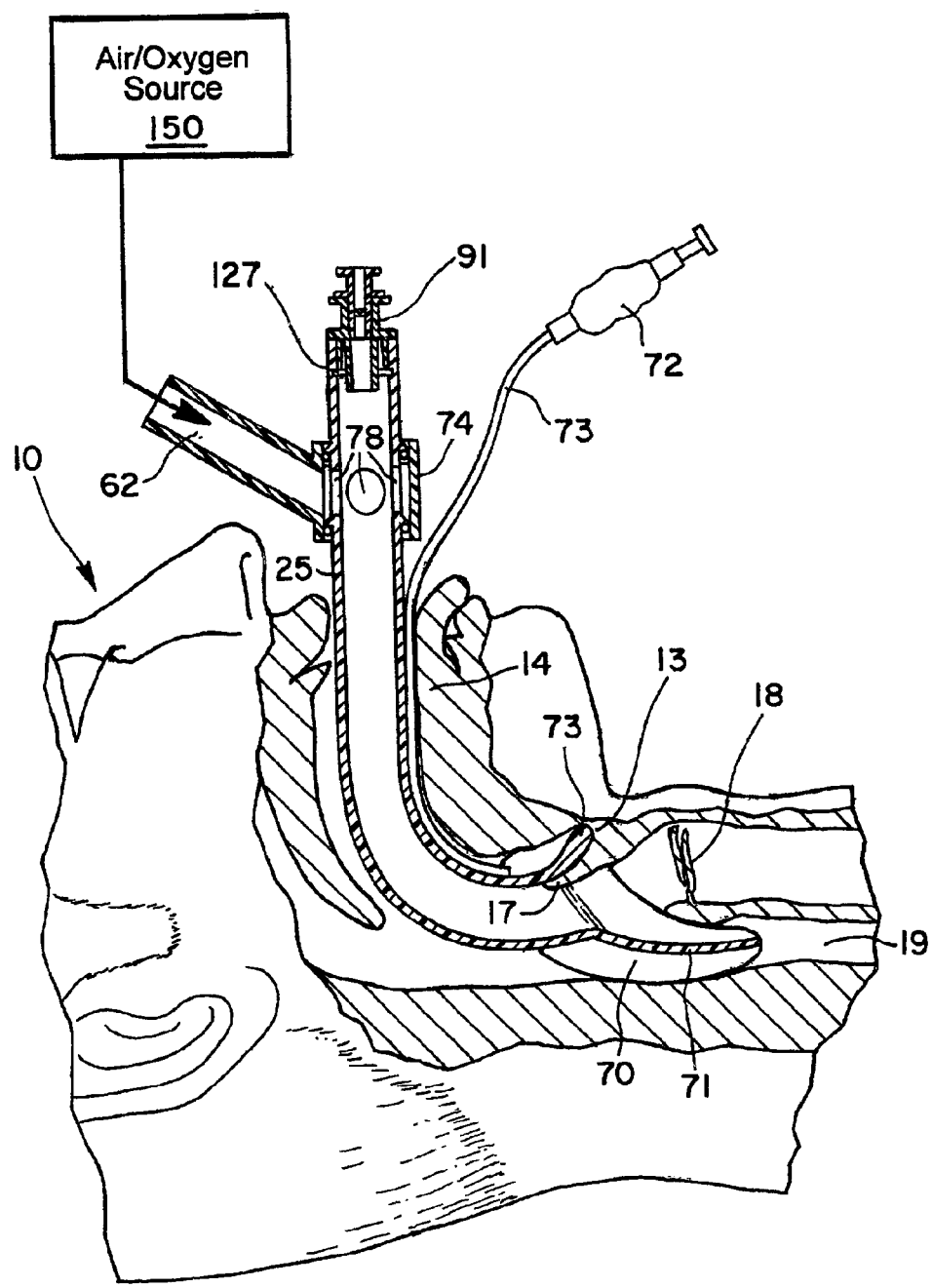
FIG. 10 is a cross-sectional view of a patient's airway after the guide 25 shown in FIGS. 7–8 has been inserted and the laryngeal mask 70 has been inflated.

Turning to FIGS. 7 and 8, front and rear perspective views are provided of an alternative embodiment of the guide 25 having a laryngeal mask 70 surrounding its distal end. The size and shape of the guide 25 are selected so that its distal portion can be readily inserted into the patient's mouth and upper airway with the laryngeal mask 70 substantially sealing the laryngeal inlet, as shown in FIGS. 9 and 10. The proximal end of the guide 25 remains outside of the patient's mouth and therefore is accessible to the healthcare provider. The guide 25 is generally J-shaped to follow the profile of a typical patient's airway through the mouth, over the tongue 14, and into the laryngopharynx just above the opening to the larynx 18 (see FIGS. 9 and 10). Preferably, the distal opening of the guide 25 is beveled to substantially match the angle of the laryngeal inlet after insertion of the laryngeal mask 70 into the patient's airway.

The laryngeal mask 70 includes a central support member 71 extending outward from the guide 25 and an inflatable member. The laryngeal mask 70 is preferably made of a soft, flexible material (e.g., a polymer or rubber) to enable it to be advanced into position without injury to the patient and to create a substantially air-tight seal about the laryngeal inlet. The degree of inflation of the laryngeal mask 70 can be adjusted through a small inflation tube 73 and air valve 72. Alternatively, the laryngeal mask 70 can be a cushion made of a soft, spongy material that is not inflatable. The laryngeal mask 70 and its support member 71 are shaped to meet several requirements. The lower portion of the laryngeal mask 70 substantially blocks the esophagus 19 to minimize the risk of regurgitation of stomach contents and the passage of air into the stomach. The upper portion of the laryngeal mask 70 guides the distal end of the guide 25 into alignment with the laryngeal inlet as the guide 25 is inserted along the patient's airway.

In the embodiment shown in the drawings, the laryngeal mask 70 is generally boot-shaped when inflated. The lower portion of the laryngeal mask 70 forms the toe of the boot, which blocks the esophagus. The lower portion of the laryngeal mask 70 also helps to align the distal opening of the guide 25 with the patient's laryngeal inlet. After the mask 70 is inflated, the upper portion of the mask 70 substantially fills the laryngopharynx at the level of the laryngeal inlet. The upper portion of the laryngeal mask 70 surrounds the laryngeal inlet so that the distal opening of the guide 25 is sealed in fluid communication with the laryngeal inlet. Thus, substantially all of the gas inhaled or exhaled by the patient passes through the guide 25. For example, the laryngeal mask 70 can be formed by injection blow molding, rotational molding, or dip molding.

The upper portion of the mask 70 surrounding the distal opening of the guide 25 is canted at an angle to complement the natural angle of the laryngeal inlet. The distal end of the guide 25 can also be beveled at this complementary angle. This enables the laryngeal mask 70 to directly engage the laryngeal inlet along the longitudinal axis of the patient's airway as the guide 25 is advanced. The shape of the upper portion of the laryngeal mask 70 further helps to guide the distal opening of the guide 25 so that it is axially aligned with the laryngeal inlet and abuts the laryngeal inlet in an end-on relationship as the guide 25 is inserted along the patient's airway. In contrast, conventional laryngeal masks typically approach the laryngeal inlet from a posterior or inferior position.

The proximal end of the guide 25 can be sealed by a removable guide cap 91 during insertion of the guide 25 and resuscitation of the patient as shown in FIGS. 9 and 10. The guide cap 91 has an outside diameter dimensioned to seat into the proximal opening of the guide 25 and thereby prevent the escape of gas through this opening. When inserted, the guide cap 91 abuts and seals against an annular seal ring 127 within the guide 25. The guide cap 91 has a small passageway or port extending vertically through the guide cap 91. As shown in FIGS. 9 and 10, a luer connector with a one-way valve (e.g., a duck-bill valve) is permanently attached to the guide cap 91 so that air or fluid can only flow down the passageway of the guide cap 91, but not up. Thus, the one-way valve serves to prevent air/oxygen from escaping through the guide 25 during resuscitation.

A syringe 55 containing anesthetic can be secured to the luer connector on the guide cap 91. As the guide 25 is advanced into the patient's mouth and hypopharynx, the healthcare provider squirts anesthetic from the syringe, through the one-way valve and guide 25 to lessen discomfort. After the guide 25 has been advanced into position, the guide cap 91 is removed from the guide 25 to allow insertion of the endotracheal tube 40 and light wand 30 through the guide 25, as will be discussed below.

A flow of air/oxygen is delivery to the patient via the guide 25 through a ventilation port 62 extending at an angle from the side of the guide 20. A rotatable collar 74 allows the ventilation port 62 to be rotated about the central axis of the guide 25 to any desired orientation. Air/oxygen flows through the ventilating port 62 into the annular space between the collar 74 and the guide 25, and through a series of ventilation holes 78 into the interior of the guide 25, as shown in FIGS. 9 and 10. For example, the ventilation port 62 can be connected to a conventional ventilator or a resuscitation bag. Alternatively, a mouthpiece can be connected to the ventilation port 62 for initial patient resuscitation by a healthcare provider.

The following is a description of a typical method of use for this embodiment of the guide 25: The curved distal portion of the guide 25 is first inserted into the patient's mouth and laryngopharynx with the laryngeal mask 70 deflated, as shown in FIG. 9. If necessary, the ventilation port 62 can be used as a hand grip during insertion of the guide 25. The lower portions of the support member 71 and laryngeal mask 70 extend into the esophagus 19. The upper portions of the support member 71 and the laryngeal mask 70 surround the laryngeal inlet.

A protrusion 73 on the anterior portion of the distal tip of the guide 25 or support member 71 is inserted to the patient's vallecula 13 (i.e., the notch between the base of the tongue 14 and the epiglottis 17). The protrusion 33 pushes on the vallecula 13, which tends to lift the epiglottis 17 from the laryngeal inlet and helps to ensure patency of the patient's airway.

After the distal portion of the guide 25 and the laryngeal mask 70 are appropriately positioned relative to the laryngeal inlet, the laryngeal mask 70 is inflated via the inflation tube 73 to establish a seal around the laryngeal inlet, as depicted in FIG. 10. The lower portion of the inflated laryngeal mask 70 substantially blocks the esophagus 19. The upper portion of the inflated laryngeal mask 70 substantially fills the laryngopharynx adjacent to the laryngeal inlet 27, and thereby seals the distal opening of the guide 25 in fluid communication with the laryngeal inlet. The side portions of the laryngeal mask 70 pinch the sides of the epiglottis 17, which also tends to lift the epiglottis 17 from the laryngeal inlet.

Optionally, a syringe containing a local anesthetic (e.g., lidocaine or xylocaine) can be connected to the luer connector on the guide cap 91 at the proximal end of the guide 25 to squirt anesthetic as the guide 25 is inserted through the patient's mouth and into the laryngopharynx. If squirted with sufficient force, the anesthetic can be carried as far as the larynx 18 to deaden any discomfort associated with insertion of the guide 25 and endotracheal tube 40.

During and after insertion of the guide 25, the patient can be resuscitated by supplying air/oxygen through the ventilation port 62. For example, the flow of air can be supplied by a resuscitation bag attached to the ventilation port 62 that is manually squeezed periodically to simulate natural breathing. Alternatively, a resuscitation attachment can be attached to the ventilation port 62 to enable a healthcare provider to directly resuscitate the patient.

After the patient's condition has been stabilized to some degree during initial resuscitation, an endotracheal tube 40 is inserted over the light wand 30 so that the distal tip of light wand is roughly adjacent to distal end 46 of the endotracheal tube 40. The guide cap 91 is removed from the proximal end of the guide 25. Resuscitation, oxygenation, or artificial ventilation continue without interruption while the light wand 30 and endotracheal tube 40 are advanced along the guide 25 and through the laryngeal mask 70 to a position within the trachea 16 past the larynx 18. The shape of the guide 25, the support member 71, and laryngeal mask 70 tend to align the distal opening of the guide 25 with the larynx 18 so that the light wand 30 and endotracheal tube 40 will pass through the opening between the vocal cords.

The seal ring 127 within the proximal end of the guide 25 has an inside diameter that is only slightly larger than the outside diameter of the endotracheal tube 40. This maintains a sufficiently tight fit around the endotracheal tube 40 to prevent the escape of gas through the seal. However, air/oxygen flows freely through the space between the endotracheal tube 40 and the surrounding guide 25 to maintain patient respiration.

After the endotracheal tube 40 and light wand 30 have been advanced through the larynx 18 and the healthcare provider observes the glow from the light source 32 through the anterior tracheal wall, the laryngeal mask 70 is deflated and the guide 25 is removed or retracted over the light wand 30 while leaving the endotracheal tube 40 and light wand 30 in place within the trachea, as previously discussed. Alternatively, the guide 25 can be left in place to serve as an oral airway and to protect the endotracheal tube 40 from being bitten by the patient's teeth. However, the laryngeal mask 70 should be deflated if the guide 25 is to be left in place in the patient's airway for an extended period time to minimize damage to the mucous lining.

Finally, the cuff 44 on the endotracheal tube 40 is inflated and the light wand 30 is removed from within the endotracheal tube 40. A ventilator 50 is connected to the proximal end of the endotracheal tube 40 to ventilate the patient, as previously discussed. Alternatively, the patient can be manually ventilated by connecting a resuscitation bag to the proximal end of the endotracheal tube 40.

Face Mask

The present invention can either be used with or without a face mask. In an operating room environment, it is often advantageous for the anesthesiologist to be able to work with both hands if an assistant is not available. The previous embodiment of this invention enables the anesthesiologist to ventilate the patient, while keeping both hands free to perform endotracheal intubation. However, in an emergency setting, rapid resuscitation of the patient is often of paramount initial importance. Thus, a need exists for an embodiment of the present invention that incorporates a face mask to initially resuscitate the patient.

Figure 11:
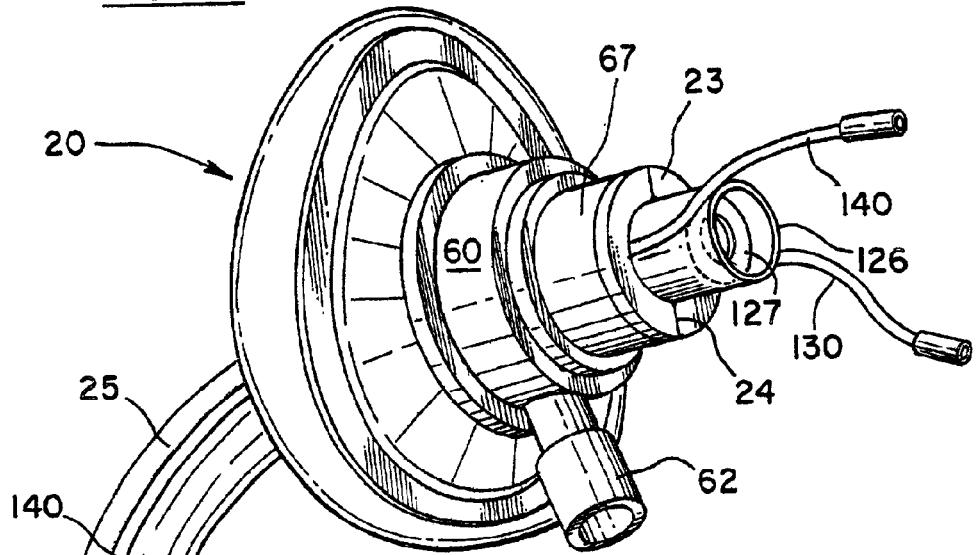
FIG. 11 is a front perspective view of another embodiment of the guide 25 incorporating a face mask 20 for initial resuscitation of the patient.
Figure 12:
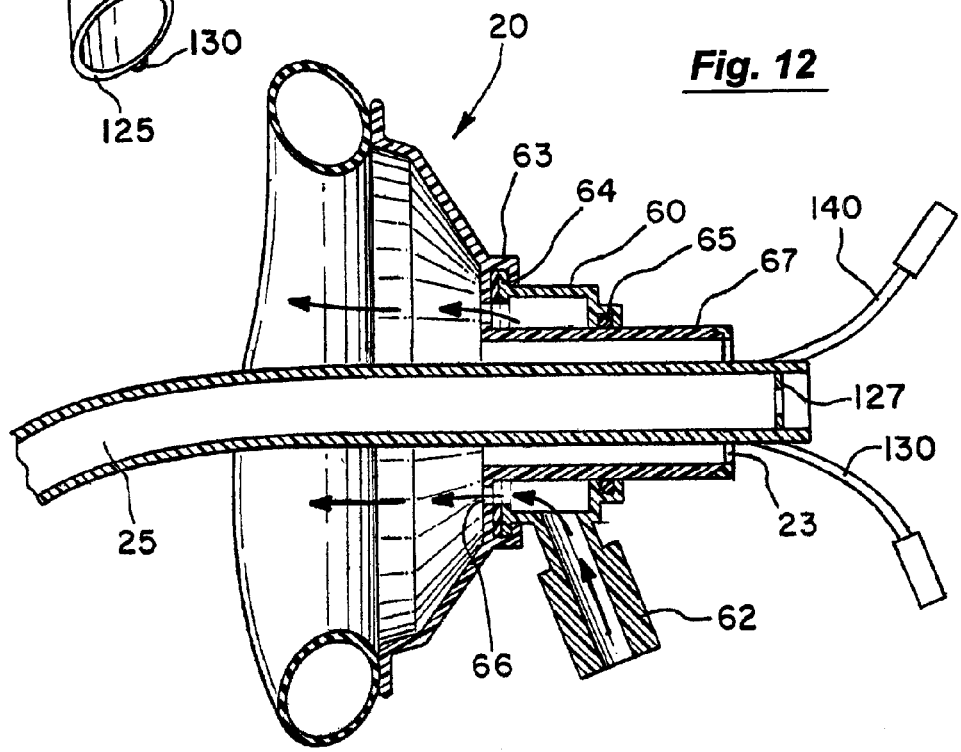
FIG. 12 is a cross-sectional view of the guide 25 and face mask 20 corresponding to FIG. 11.

FIGS. 11 through 12 show an embodiment of the present invention that includes a face mask 20 for initial resuscitation of the patient. FIG. 11 is a front perspective view of the guide 25 and face mask 20. FIG. 12 is a cross-sectional view of the guide 25 and face mask 20 corresponding to FIG. 11. The face mask 20 is adapted to fit over the patient's mouth and nose for resuscitation of the patient 10. The mask 20 has a low profile and is made of an elastic material, such as rubber or flexible plastic, to allow the mask to conform to the contours of the patient's face and create a more air-tight seal around the mouth and nose.

The face mask 20 includes a resealable port 23. In the preferred embodiment, the face mask port 23 consists of a flexible, elastic membrane having a stretchable opening 24 with dimensions large enough to allow the guide 25 to pass through the face mask port 23. For example, this elastic membrane can be made of rubber with slot or hole forming an opening 24, as shown in FIG. 11.

As depicted in FIGS. 11 and 12, the guide 25 can be readily inserted through the face mask port 23 while maintaining a substantially air-tight seal around the guide 25 to prevent gas from escaping from within the face mask 20. The guide 25 extends posteriorly through the face mask 20 so that its curved distal portion is inserted into the patient's mouth and hypopharynx as the face mask 20 is placed over the patient's mouth. The face mask port 23 allows the guide 25 to slide relative to the face mask 20, and also allows a limited range of rotation of the guide 25. This flexibility allows the guide 25 to accommodate a wide range of patient sizes and conditions.

For example, a flow of air can be supplied by a resuscitation bag attached to the mask 20 that is manually squeezed periodically to simulate natural breathing. However, other conventional air/oxygen supplies for resuscitation could be substituted at the resuscitation connector 62 for the face mask 20. In the preferred embodiment, the flow of oxygen/air from the resuscitation bag is directed around the exterior of the curved guide 25, as depicted in FIG. 12. This tends to inflate the patient's mouth and airway, which distends the collapsible tissues, and thereby makes visualization and insertion of the endotracheal tube 40 easier.

The face mask assembly 20 includes a rotatable annular ventilation collar 60 with a ventilation port 62 that can be connected to a conventional respiration bag or other air/oxygen source to ventilate the patient. The ventilation collar 60 allows the ventilation port 62 to be freely rotated to any desired orientation about the face mask port 23. Air from the resuscitation bag flows through the ventilation port 62 and into the annular ventilation collar 60. It then flows through a plurality of small ventilation holes 66 in the mask 20 beneath the annular ventilation collar 60 into the patient's mouth and nose. In particular, the mask 20 includes a raised cylindrical flange 63 that engages a corresponding flange 64 extending around the base of the annular ventilation collar 60 to provide a rotatable, but generally airtight seal between the mask 20 and the ventilation collar 60. A tubular member 67 extends upward from the surface of the mask 20 beneath the ventilation collar 60, and passes through the central opening in the annular ventilation collar 60. An O-ring 65 provides a rotatable, airtight seal between the outer surface of the tubular member 67 and the ventilation collar 60, and also serves to retain the ventilation collar 60 in place on the mask assembly 20.

After the patient's condition has been stabilized to some degree during initial resuscitation, the light wand 30 is inserted through an endotracheal tube 40 until the distal tip of the light wand 30 is adjacent to the distal end 46 of the endotracheal tube, as previously discussed. The light wand 30 and endotracheal tube 40 are then inserted through the guide 25 to a position within the trachea 16 past the larynx 18 while resuscitation continues, as previously discussed. After the endotracheal tube 40 has been inserted, the face mask 20 and guide 25 can be removed while leaving the endotracheal tube 40 and light wand 30 in place within the trachea 16. As previously discussed, the healthcare provider can monitor the location of the light at the distal tip of the light wand 30 to ensure that the endotracheal tube 40 remains in its proper position.

The loose fit provided by the seal ring 127 within the proximal end of the guide 25 allows the face mask 20 and guide 25 to be withdrawn over the connector 42 at the proximal end of the endotracheal tube 40 with minimal effort and dislocation of the endotracheal tube 40. The position of the endotracheal tube 40 can be stabilized while the mask 20 is removed by manually gripping the proximal end of the endotracheal tube 40 and gradually urging it through the proximal end of the guide 25 as the mask 20 and guide 25 are lifted from the patient's face. The physician can then reach under the face mask 20 to grip the endotracheal tube 40 after the mask 20 and guide 25 have been lifted sufficiently to allow access. Alternatively, the face mask 20 can be removed while leaving the guide 25 in place to serve as an oral airway and to protect the endotracheal tube 40 from being bitten by the patient's teeth. The light wand 30 can then be withdrawn from within the endotracheal tube 40. The cuff 44 at the distal end 46 of the endotracheal tube 40 is inflated through the port valve 45 to block the trachea 16 and a ventilator 50 is attached to the endotracheal tube 40, as previously discussed.

Stabilizer

FIG. 13 is a perspective view of a stabilizer 220 that can be attached to the light wand 30 and then used to advance the endotracheal tube 40 along the guide 25 and into the patient's trachea. In the preferred embodiment, the stabilizer 220 is a flexible plastic tube having a C-shaped cross-section that can be readily clipped over the light wand 30 at any desired location along its length. The inside diameter of the stabilizer 220 should be selected to provide a snug, frictional fit against the exterior of the light wand 30 so that the stabilizer 220 will not readily slide after it has been attached to the light wand 30. The stabilizer 220 can also be readily removed from the light wand 30 by the healthcare provider for cleaning or to adjust its location on the light wand 30. The stabilizer 220 should have outside dimensions sufficiently large to push the endotracheal tube 40 forward as the light wand 30 is advanced by the healthcare provider.

The proximal end of the endotracheal tube 40 can be fitted with a removable cap 230 shown in FIG. 14. This cap 230 has outside dimensions selected so that it can be inserted snugly into the proximal opening of the endotracheal tube 40 and yet is sufficiently small to fit through the guide 25, if necessary.

A central passageway extends axially through the cap 230 to receive the light wand 30. The light wand 30 passes freely through the cap 230. However, the cap passageway has an inside diameter smaller than the stabilizer 220, so that the stabilizer 220 will abut and push against the proximal end of the endotracheal tube 40 as the light wand 30 is advanced by the healthcare provider. In effect, the stabilizer 220 and cap 230 serve to removably attach the proximal end of the endotracheal tube 40 at a desired position on the wand 30 so that the light source 32 is adjacent to the distal end of the endotracheal tube 40, prior to advancing the wand 30 and endotracheal tube 40 along the guide 25.

In practice, this embodiment of the present invention typically uses the following sequence of steps: The stabilizer 220 is attached at a desired position on the light wand 30. The light wand 30 is then inserted into the proximal end of the endotracheal tube 40 until the stabilizer 220 abuts the proximal end of the endotracheal tube 40. The location of the stabilizer 220 on the light wand 30 is normally selected so that the distal tip of the light wand 30 will extend slightly beyond the distal tip 46 of the endotracheal tube 40.

Optionally, a removable cap or adapter 230 is attached to the proximal end of the endotracheal tube 40 prior to insertion of the light wand 30 so that the stabilizer 220 will push against this cap 230 as the healthcare provider advances the light wand 30. In this variation, the light wand 30 is inserted through both the endotracheal tube cap 230 and the endotracheal tube 40. This cap or adapter 230 has dimensions allowing the guide 25 to be retracted over the adapter 230, endotracheal tube 40, and the flexible member of the wand 30.

In addition, the cap 230 can be equipped with a plurality of splines to grip the flexible member of the wand 30. In this embodiment, the cap 230, by itself, can be used to removably secure the proximal end of the endotracheal tube 40 relative to the light wand 30. The splines allow the stabilizer 220 to be omitted, if desired.

Figure 15:
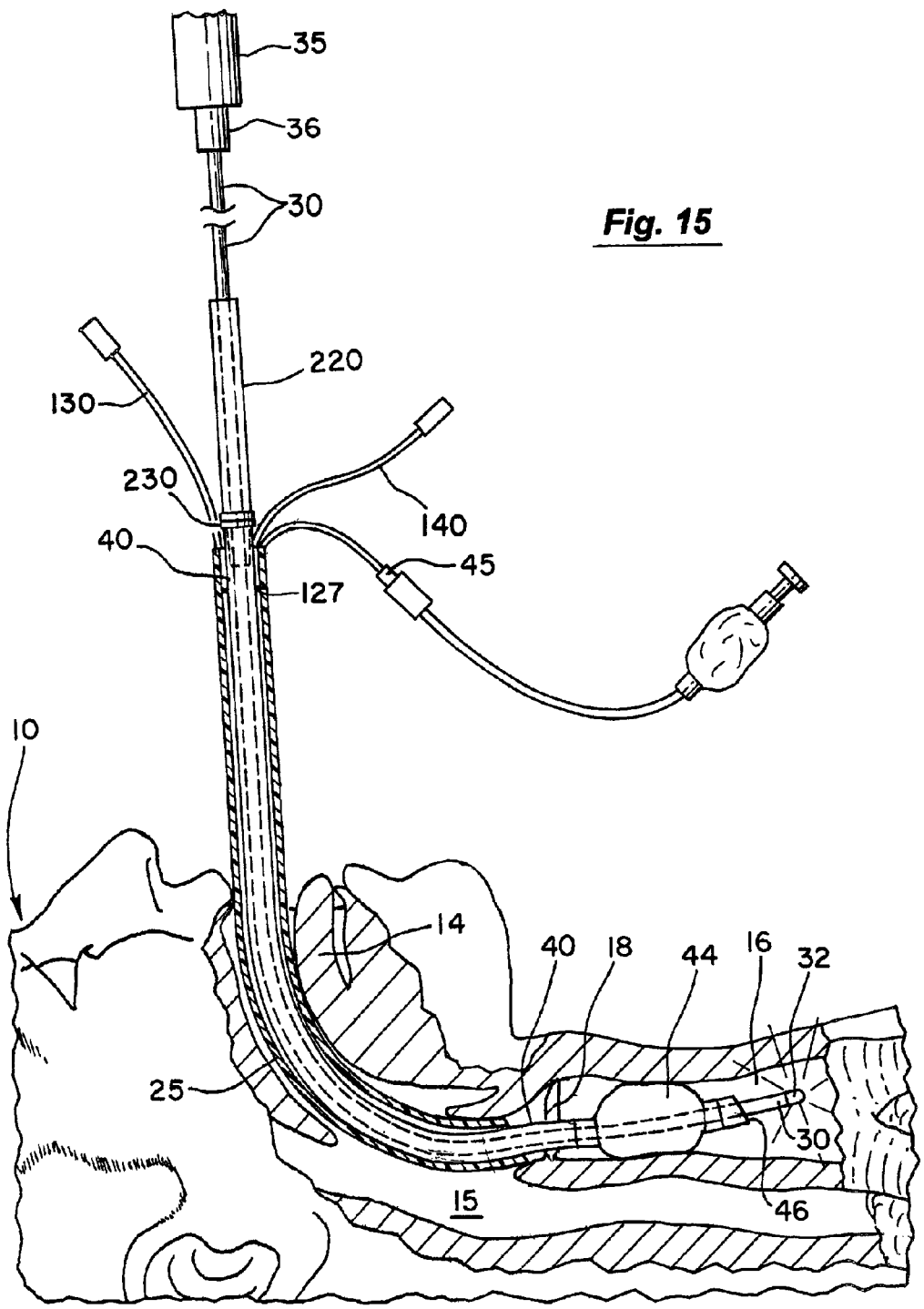
FIG. 15 is a cross-sectional view of a patient's mouth and airway showing how the stabilizer 220 and endotracheal tube cap 230 can be used to advance the light wand 30 and endotracheal tube 40 along the guide 25 and the patient's airway to a position below the larynx 18.

The guide 25 is inserted into the patient's airway, as previously discussed. The assembly consisting of the endotracheal tube 40, light wand 30 and stabilizer 220 is then inserted through the proximal end of the guide 25. The healthcare provider pushes forward on the light wand 30 to advance the endotracheal tube 40 and the light wand 30 along the guide 25 and into the patient's trachea 16 until the light 32 becomes visually observable through the anterior tracheal wall as shown in FIG. 15. The guide 25 is then removed over the proximal end of the endotracheal tube 40 while leaving the endotracheal tube 40 and light wand 30 in place. The light wand 30 is then withdrawn from within the endotracheal tube 40 and the endotracheal tube cap 230 is removed if one is present. Finally, the patient can be ventilated via a ventilator 50 connected to the endotracheal tube 40.

The above disclosure sets forth a number of embodiments of the present invention. Other arrangements or embodiments, not precisely set forth, could be practiced under the teachings of the present invention and as set forth in the following claims.

I claim:

1. A method for intubating a patient with an endotracheal tube comprising:
    inserting a curved tubular guide into a patient's mouth and upper airway, so that the distal end of the guide is positioned above the patient's larynx;
    providing a light wand having a flexible elongated member with a light source at its distal tip;
    inserting the wand through an endotracheal tube, so that the light source at the distal tip of the wand is adjacent to the distal end of the endotracheal tube;
    advancing the wand and endotracheal tube along the guide until the distal end of the endotracheal tube passes through the patient's larynx and the light source is eternally observable at a predetermined location through the patient's tracheal wall;
    retracting the guide over the proximal end of the endotracheal tube while leaving the wand and endotracheal tube in place in the patient's airway; and
    withdrawing the wand from within the endotracheal tube while leaving the endotracheal tube in place in the patient's airway.

2. The method of claim 1 further comprising the step of removably attaching the proximal end of the endotracheal tube at a desired position on the wand, prior to the step of advancing the wand and endotracheal tube along the guide.

3. The method of claim 1 wherein the wand further comprises a removable handle, and further comprising the step of removing the handle of the wand after the step of advancing endotracheal tube and wand, so that the guide can be removed over the proximal end of the wand.

4. The method of claim 1 further comprising supplying air/oxygen to the patient through the guide during intubation.

5. An apparatus for intubating a patient with an endotracheal tube, said apparatus comprising:
    a light wand having an elongated flexible member with a distal tip and a light source at the distal tip of the flexible member, said flexible member having dimensions to fit through an endotracheal tube with the light source of the wand adjacent to the distal end of the endotracheal tube; and
    a curved tubular guide for insertion into a patient's mouth and upper airway, having a distal end positioned above the patient's larynx; wherein the wand and endotracheal tube can be advanced along the guide so that the distal end of the endotracheal tube passes through the patient's larynx and the light source is externally observable at a predetermined location through the patient's tracheal wall.

6. The apparatus of claim 5 wherein the wand has sufficient length to allow the guide to be retracted over the wand while leaving the endotracheal tube in place in the patient's airway.

7. The apparatus of claim 5 wherein the light wand further comprises a removable handle at the proximal end of the flexible member allowing the guide to be removed over the flexible member of the light wand.

8. The apparatus of claim 5 further comprising an adapter for removably attaching the proximal end of an endotracheal tube to a desired position on the flexible member of the wand.

9. The apparatus of claim 8 further comprising a cap insertable into the proximal end of an endotracheal tube to engage the adapter.

10. The apparatus of claim 9 wherein the cap further comprises a plurality of splines to grip the flexible member of the wand.

11. The apparatus of claim 8 wherein the light wand further comprises a timer providing an indicia triggered a predetermined time period following activation of the light source.

12. An apparatus for intubating a patient with an endotracheal tube, said apparatus comprising:
    a light wand having an elongated flexible member with a distal tip and a light source at the distal tip of the flexible member, said flexible member having dimensions to fit into an endotracheal tube;
    a curved tubular guide for insertion into a patient's mouth and upper airway, having a distal end positioned above the patient's larynx; and
    an adapter for adjustably attaching the proximal end of an endotracheal tube at a location on the flexible member of the wand so that the light source of the wand is adjacent to the distal end of the endotracheal tube; wherein the wand and endotracheal tube can be advanced along the guide so that the distal end of the endotracheal tube passes through the patient's larynx and the light source is externally observable at a predetermined location through the patient's tracheal wall; and wherein the adapter has dimensions allowing the guide to be retracted over the adapter, endotracheal tube, and the flexible member of the wand.

13. The apparatus of claim 12 wherein the flexible member of the wand has sufficient length to allow the guide to be retracted over the wand while leaving the endotracheal tube in place in the patient's airway.

14. The apparatus of claim 12 wherein the wand further comprises a removable handle at the proximal end of the flexible member allowing the guide to be removed over the flexible member of the light wand.

15. The apparatus of claim 12 further comprising a cap insertable into the proximal end of an endotracheal tube to engage the adapter.

16. The apparatus of claim 15 wherein the cap further comprises a plurality of splines to grip the flexible member of the wand.

17. The apparatus of claim 12 wherein the light wand further comprises a timer providing an indicia triggered a predetermined time period following activation of the light source.

* * * * *